United States Patent [19]

Bailey

[11] 4,181,130
[45] Jan. 1, 1980

[54] DROP DISCRIMINATOR SYSTEM

[75] Inventor: Wilber H. Bailey, Leucadia, Calif.

[73] Assignee: Ivac Corporation, San Diego, Calif.

[21] Appl. No.: 848,567

[22] Filed: Nov. 4, 1977

[51] Int. Cl.² .................................................. A61M 5/16
[52] U.S. Cl. ........................ 128/214 E; 128/DIG. 13
[58] Field of Search .......... 128/2.05 F, 214 E, 214 F; 73/194 R, 196, 207, DIG. 11; 340/526, 603, 605, 606, 609, 619, 620

[56] References Cited

U.S. PATENT DOCUMENTS

| | | | |
|---|---|---|---|
| 3,340,386 | 9/1967 | Hurst | 73/194 R |
| 3,618,061 | 11/1971 | Livers | 340/606 |
| 3,669,540 | 6/1972 | Capellaro | 356/104 |
| 3,754,220 | 8/1973 | Setamler et al. | 128/2.05 F |
| 3,831,039 | 8/1974 | Henschel | 340/526 |
| 3,867,613 | 2/1975 | Schoon | 250/222 PC |
| 3,890,968 | 6/1975 | Pierce et al. | 128/214 E |
| 3,935,876 | 2/1976 | Massie et al. | 128/214 F |
| 4,000,801 | 1/1977 | Moulet | 340/606 |
| 4,038,982 | 8/1977 | Burke et al. | 128/214 E |
| 4,075,462 | 2/1978 | Rowe | 250/222 PC |
| 4,105,028 | 8/1978 | Sadlier et al. | 128/214 E |
| 4,114,144 | 9/1978 | Hyman et al. | 128/214 E |

*Primary Examiner*—William E. Kamm
*Attorney, Agent, or Firm*—Fulwider, Patton, Rieber, Lee & Utecht

[57] ABSTRACT

An electronic method and apparatus for evaluation of the quality of drop detection in apparatus for parenteral administration of medical fluids, wherein the waveforms of electrical signals representing drop flow detection are evaluated for conformity with both prescribed amplitude and time duration characteristics. Separate counters record the total number of drop events evaluated and the portion of the total which are determined to be non-conforming, and the latter counter triggers alarms if a predetermined limit is exceeded within a prescribed number of total events.

43 Claims, 8 Drawing Figures

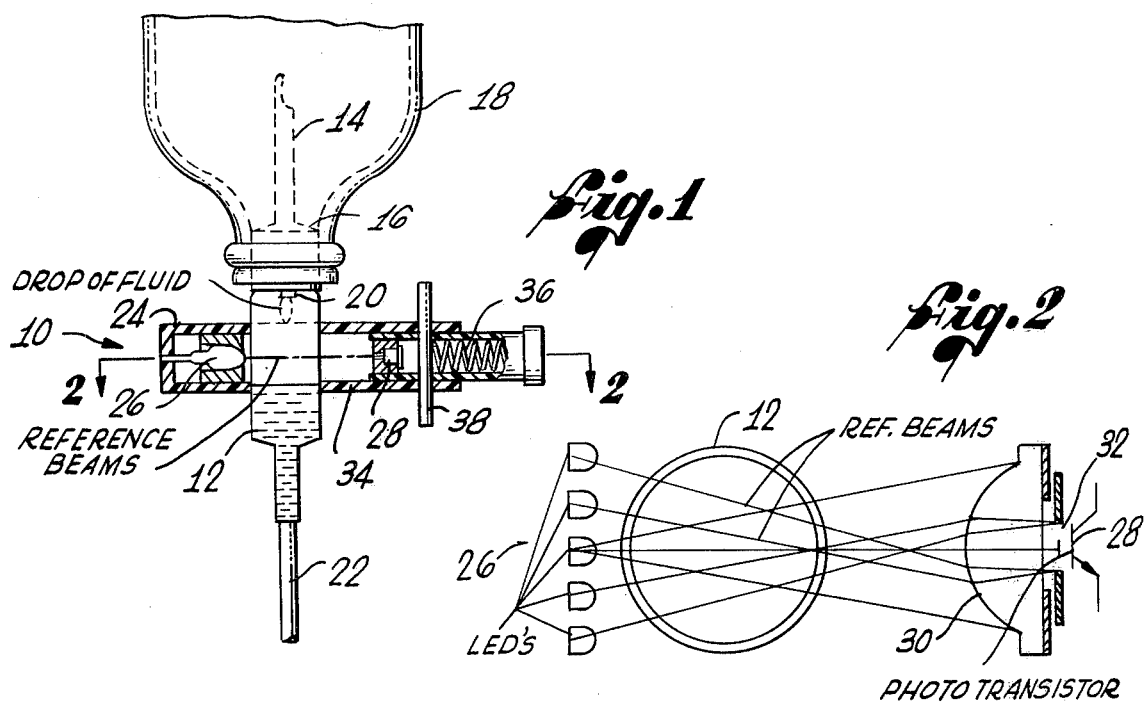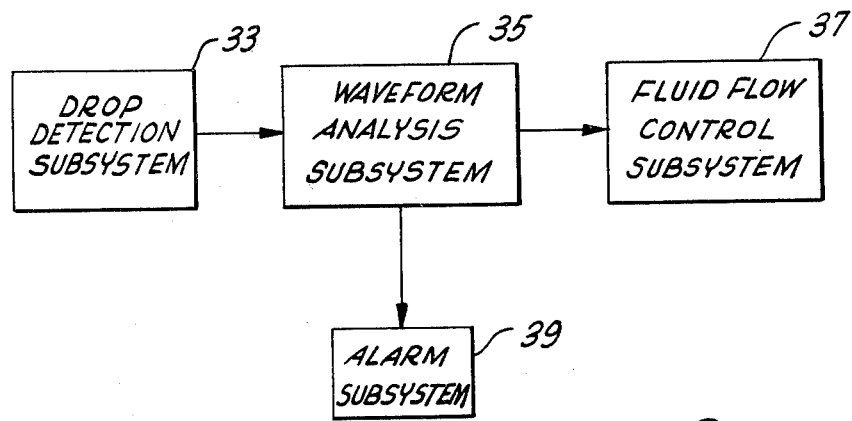

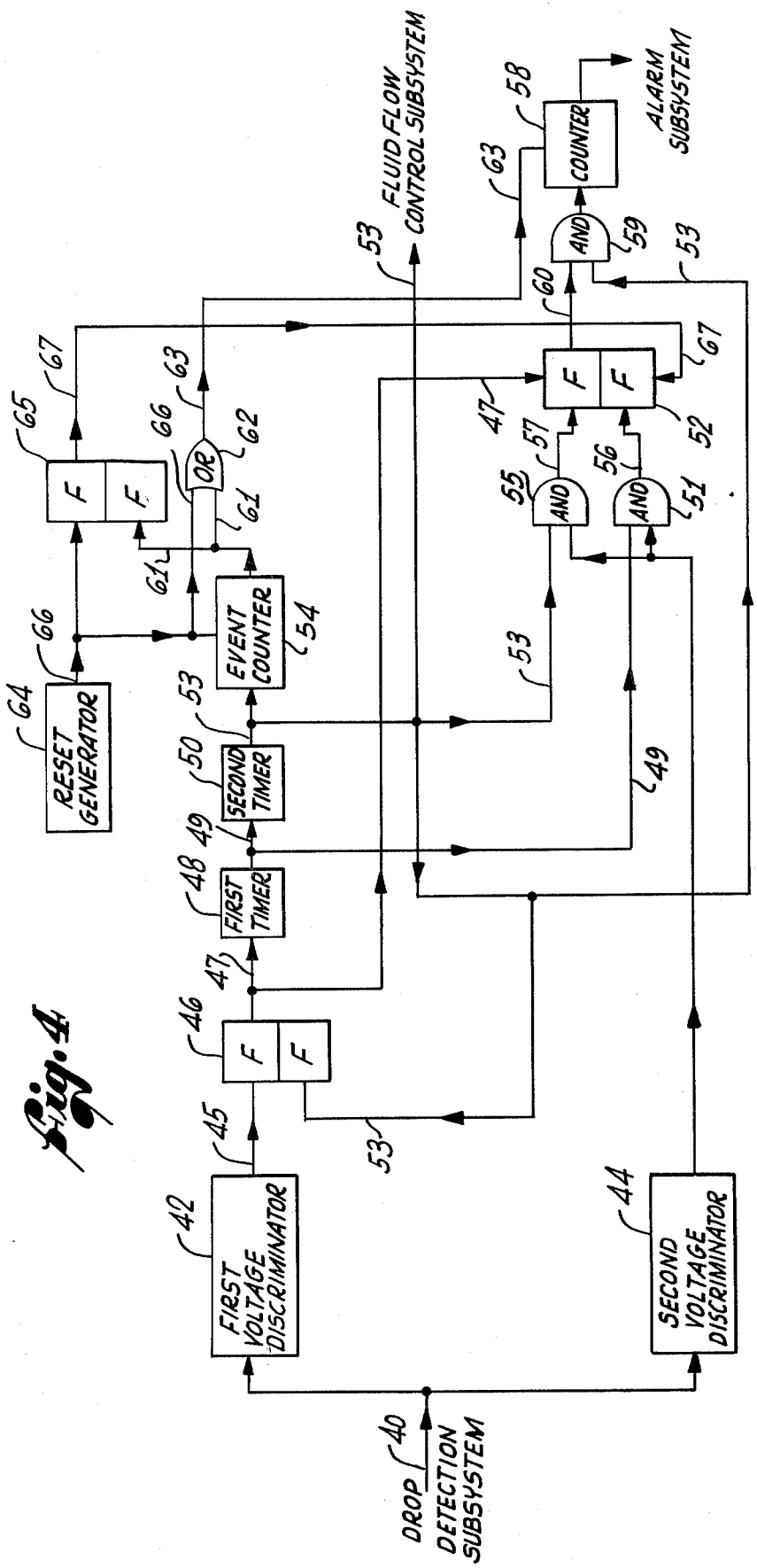

DROP DISCRIMINATOR SYSTEM

BACKGROUND OF THE INVENTION

This invention relates generally to improvements in methods and apparatus for measurement of drop flow in intravenous fluid flow control systems and, more particularly, to a new and improved drop discriminator system for accurate and reliable detection of drops falling in the drip chamber of an intravenous set or the like used in medical applications.

The usual medical procedure for the gradual parenteral administration of liquids into the human body, such as liquid nutrients, blood or plasma, makes use of apparatus which is commonly referred to in the medical arts as an intravenous administration set, or simply intravenous set. The intravenous set usually comprises a bottle of liquid, normally supported in an inverted position, an intravenous feeding tube, typically of clear plastic, and a suitable valve mechanism, such as a roll clamp, which allows for liquid to drip out of the bottle at a selectively adjustable rate into a transparent drip chamber below the bottle. The drip chamber serves the dual function of allowing a nurse or other attendant to observe the rate at which the liquid drips out of the bottle and also creates a reservoir for the liquid at the lower end of the drip chamber to ensure that no air enters the main feeding tube leading to the patient.

While observation of the rate of drop flow via the drip chamber is a simple way of controlling the amount of liquid fed to a patient over a period of time, its ultimate effectiveness requires that a relatively constant vigil be maintained on the drop flow, lest it cease entirely due to exhaustion of the liquid supply or become a continuous stream and perhaps increase the rate of liquid introduction to the patient to a dangerous level.

By way of example, it has been the general practice in hospitals to have nurses periodically monitor drop flow rate at each intravenous feeding or parenteral infusion station. Such monitoring of drop flow rate is a tedious and time-consuming process, prone to error and associated, possibly serious consequences, and resulting in a substantial reduction of the available time of qualified medical personnel for other important duties. Typically, the nurse monitoring drop flow rate will use a watch to time the number of drops flowing in an interval of one or more minutes, and she will then mentally perform the mathematics necessary to convert the observed data to an appropriate fluid flow rate, e.g., in cubic centimeters per hour or drops per minute. If the calculated flow rate is substantially different than the prescribed flow rate, the nurse must manually adjust the roll clamp for a new rate, count drops again, and recalculate to measure the new rate.

In recent years, a number of electrical monitoring systems, drop flow controllers and infusion pumps of both the peristaltic and the syringe types have been developed to accomplish the various tasks of sensing and regulating the parenteral administration of liquids into the human body. Some of these devices have also been capable of activating alarms when a potentially dangerous condition exists, thus freeing medical personnel to some extent for other duties. A primary object of many of these devices is precise monitoring and regulation of the drop flow rate itself and, obviously, accurate and reliable detection of falling drops is fundamental to the proper operation of such devices. In other of these devices, such as syringe pumps, falling drops may be detected only for the purpose of guarding against potentially dangerous conditions. Even in the latter case, however, it is apparent that reliable detection of drop flow is a matter of concern.

Typically, a drop sensor is used with the aforementioned devices to monitor drop flow directly at the drip chamber of an intravenous set. The drop sensor may include a sensor housing containing a photocell-monitoring device. The sensor housing is appropriately clamped to the transparent drip chamber with a light source and a photocell positioned on opposite sides thereof. A falling drop of fluid within the drip chamber interrupts the reference beam created by the light source, and the variation in the electrical response of the photocell is communicated to appropriate circuitry indicating the presence of a drop. The housing typically includes a releasable clamping mechanism for ease of installation and removal of the drop sensor with respect to drip chambers of various configurations. This releasable clamp is a desirable feature because the drop sensor may be used with many different configurations of drip chambers.

A variety of problems are created, however, because of the variability in different intravenous sets and the potential for human error in positioning the drop sensor on the drip chamber. The first problem is that different intravenous sets are designed to produce drops of various sizes, which can result in variations in the electrical response of the photocell to the presence of the drop. A second, more serious problem is that medical personnel can position the drop sensor too high on the drip chamber, whereby the drops intercept the reference beam during initial drop formation, or too near the top of the fluid reservoir, whereby splash and ripple from the falling drops create artifacts in the electrical response of the photocell. A still further problem is the possibility that the drip chamber may become tilted such that the drops fall very near the side of the drip chamber, occluding a smaller portion of the reference light beam than usual and thereby resulting in an abnormally small electrical response to the drop.

In each of the foregoing situations, waveforms of the resulting electrical responses of the photocell may differ greatly from the waveforms that normally result from a correctly positioned drop sensor on a drip chamber producing a predetermined drop size. For instance, these waveforms may have leading edges with abnormally slow rise times and result in long pulse durations, or an oscillatory effect may result which appears to be indicative of a plurality of falling drops, or the waveforms may have low amplitudes. The result can be an erroneous indication of drop flow rate and interference with proper operation of the parenteral administration devices to which the drop sensor is connected.

Hence, those concerned with the development and use of parenteral fluid administration systems have long recognized the need for a reliable and accurate system for sensing drop flow which obviates the aforedescribed difficulties. The present invention clearly fulfills this need.

SUMMARY OF THE INVENTION

Briefly, and in general terms, the present invention provides a new and improved drop discriminator system for indicating whether drop flow activity in an intravenous administration set is being detected accurately and reliably. Basically, the invention is directed to an improved electronic method and apparatus for evaluating the waveforms of the electrical signals that are generated in response to the detection of drop flow activity in the drip chamber to determine conformity with prescribed waveform characteristics and to indicate a need, when appropriate, for repositioning of the drop sensor or the drip chamber, or both.

In a presently preferred embodiment, by way of example, a drop detection subsystem generates electrical signals which are representative of the drop flow activity in a drip chamber as detected by the drop sensor. Both the voltage amplitude and time duration of these electrical signals are analyzed for conformity with characteristics normally expected of accurately detected drops. Nonconformity in these electrical signals, beyond an allowable tolerance for transient fluctuations, causes an alarm to trigger and shuts off the parenteral administration device.

More particularly, with reference to the preferred embodiment, the voltage amplitude of each electrical signal is analyzed during first and second adjoining time frames and, no later than the end of the second time frame, a decision is made as to the acceptability of the drop detection event. Specifically, a first voltage amplitude discriminator is utilized to detect the occurrence of sufficient drop flow activity, as represented by the electrical signal, to indicate a drop event and thereby initiate the aforementioned waveform analysis. Minor perturbations in the electrical signals are expected and can be tolerated without significant loss of reliability in the detection of drop flow. When a drop event does occur, the first voltage amplitude discriminator triggers a timer which begins the first time frame for evaluation of the waveform. At the same moment, a decision flip-flop is set to its "true" state, indicating that the drop event detection is considered initially unacceptable pending further evaluation.

A second voltage amplitude discriminator of higher threshold than the first discriminator monitors the electrical signal during the first time frame to determine whether its voltage amplitude exceeds the minimum amplitude expected of an acceptable drop event. If this higher threshold, which is characteristic of an acceptable drop event in the drop detection subsystem being utilized, is reached during the first time frame, the decision flip-flop is reset to its "false" state thereby indicating conditional acceptability of the detection, pending further evaluation during the second time frame. Failure to reach this higher threshold during the first time frame automatically results in rejection of the drop detection event as unacceptable at the end of the second time frame. Inadequate signal amplitude in the first time frame might occur when the drip chamber is tilted so that less than a normal portion of the reference beams are occluded upon the falling of a drop.

During the second time frame, it is anticipated that all significant perturbations in the electrical signals have subsided in the case of an acceptable drop detection event. To verify this condition, the second voltage amplitude discriminator is also used for continuous monitoring of the voltage amplitude of the electrical signals during the second time frame. If the threshold of the second voltage amplitude discriminator is exceeded, the drop detection event is considered unacceptable, and the second discriminator sets the decision flip-flop to its "true" state again. Such a situation has been known to occur when the drop sensor is positioned too high on the drip chamber so that drops forming in the optical sensing gap produce an electrical signal of long duration, as well as when the drop sensor is positioned so near the fluid reservoir that the electrical signal oscillates as a result of splash or ripple.

Separate counters are maintained to record the total number of drop events evaluated and the portion of the total which are determined to be unacceptable, as indicated by the state of the decision flip-flop at the end of the second time frame. The occurrence of a prescribed number of unacceptable drop detection events within a predetermined total number of events analyzed, results in the triggering of an alarm and shuts off the fluid flow control apparatus. Hence, medical personnel will be given an indication that adjustment of the drop sensor or the drip chamber, or both, is needed. As a protection against alarming during tolerable transient fluctuations in the quality of drop detection, as for instance when the parenteral administration device is being moved, more than one unacceptable drop detection in a predetermined number of detection events must occur before the system will consider the possibility of alarming.

It will be appreciated that this drop discriminator system is also effective to discover defectively formed drops, as well as irregularities in the detection system, and to indicate excessive fluid delivery rates which could result in multiple drops occurring during the first and second time frame evaluations. In this latter regard, the present invention may operate as a backup alarm system for out-of-limit alarm features already present in the parenteral administration equipment with which it operates.

The new and improved drop discriminator system of the present invention is very effective to ensure accurate and reliable detection of unacceptable drop flow activity. The system minimizes the possibility of incorrect positioning of the drop sensor on the drip chamber and is quick to inform medical personnel of any irregularities in drop detection which might pose a hazard to the patient.

The above and other objects and advantages of the invention will become apparent from the following more detailed description, when taken in conjunction with the accompanying drawings of illustrative embodiments.

DESCRIPTION OF THE DRAWINGS

FIG. 1 is an elevational view, partly in section, illustrating a drop-sensor installed on a conventional intravenous set;

FIG. 2 is an enlarged, schematic representation of a portion of a view taken along the line 2—2 in FIG. 1;

FIG. 3 is a block diagram of a drop discriminator system in accordance with the present invention;

FIG. 4 is a block diagram of a drop discriminator system in accordance with a presently preferred embodiment of the invention.

DESCRIPTION OF THE PREFERRED EMBODIMENT

Figure 5A:
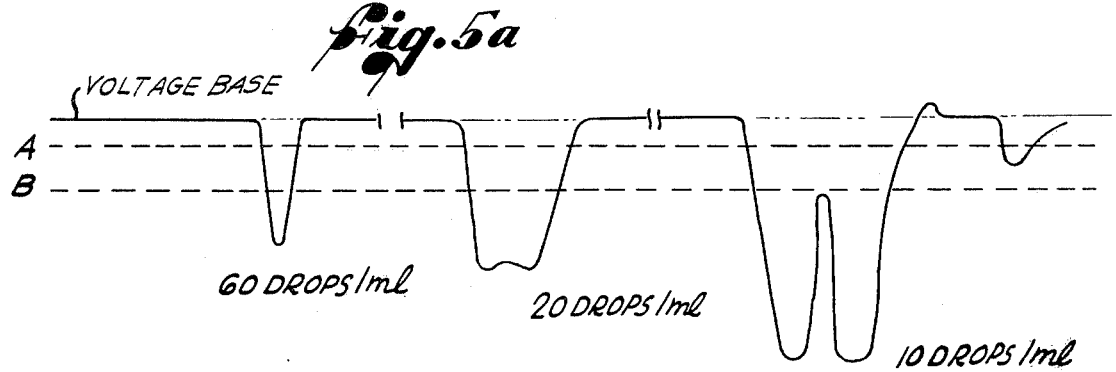
FIGS. 5a–d are waveforms of various electrical signals representative of drop flow activity in the drip chamber of an intravenous administration set.

Referring now to the drawings, and particularly to FIGS. 1–2 thereof, there is shown a new and improved system for drop discrimination and the environment in which it operates. In the ensuing description, reference will be made to the term "I.V." normally connoting intravenous administration, although it is to be understood that this is by way of example only, and the drop discriminator system of the present invention has application to other forms of parenteral administration as well as intravenous administration.

In order to sense and regulate the intravenous administration of liquids into the human body, it is necessary to continuously monitor the actual fluid flow as it occurs in an I.V. administration set. As shown in FIG. 1, this can be accomplished by mounting a drop sensor 10 upon a transparent drip chamber 12 having a hollow spike 14 at one end which pierces and extends through the stopper 16 of an inverted bottle of liquid 18. The drip chamber 12 includes a cannula 20 within its upper end to transform fluid flow through the spike 14 into drops of a predetermined size, which then fall into a reservoir of liquid at the lower end of the drip chamber and flow down an intravenous feeding tube 22. An appropriate parenteral administration device (not shown), such as a drop flow controller or peristaltic infusion pump, may manipulate the feeding tube 22 to regulate drop flow rate.

The drop sensor 10 monitors drop flow in the drip chamber 12 and includes a sensor housing 24 containing a plurality of reference light sources 26 located at a fixed distance from a photocell 28 to define a relatively narrow optical sensing gap therebetween, with the reference light beams impinging upon the photocell. The sensor housing 24 is appropriately clamped to the drip chamber 12 with the latter element positioned in the sensing gap to intercept the reference beams. Preferably, the sensing gap is located approximately mid-way between the top of the fluid reservoir at the lower end of the rip chamber 12 and the drop-forming cannula 20 in the upper end thereof. A falling drop of fluid within the drip chamber 12 interrupts the reference beams, and the variation in the electrical response of the photocell 28 is communicated to appropriate circuitry, included in the drop detection subsystem of FIG. 3, indicating the presence of a drop.

As shown more clearly in FIG. 2, the reference light sources 26 are laterally dispersed along one side of the drip chamber 12 and direct the reference beams as intersecting diagonals in a cross-fire pattern through the drip chamber at the photocell 28 to minimize the possibility of a drop falling undetected. Light-emitting diodes are typically used for the light sources, and a photo transistor is schematically shown positioned behind a lens 30 which tends to focus the reference beams through an aperture 32 in front of the phototransistor. It will be apparent that sources of illumination other than light-emitting diodes, such as grain of wheat lamps or other miniature light sources, may also be used in any suitable reference light beam array.

Also shown in FIG. 1 is a releasable clamping mechanism included with the sensor housing 24, comprising a slidable sleeve 34 biased by a spring 36 which can be actuated by a rod 38 extending outwardly from opposite sides of the sleeve. A similar drop sensor housing and releasable clamping mechanism are described in U.S. Pat. No. 3,596,515, assigned to IVAC Corporation, which description is incorporated herein by reference as though set forth in full. The releasable clamp is included for ease of installation and removal of the drop sensor with respect to drip chambers of various configurations. However, other well known clamping arrangements for mounting a suitable drop sensor upon a drip chamber may be utilized.

In addition, while a photocell monitoring device is ideally suited for the drop sensor 10, it will be appreciated that any drop sensing device capable of providing an electrical indication of the presence of a drop may be used without departing from the spirit and scope of the invention.

The drop detection subsystem 33 shown in FIG. 3 includes the drop sensor 10 and conventional circuitry to generate an electrical signal representative of the drop flow activity detected by the drop sensor. A representative set of electrical signal waveforms which may be generated by this drop detection subsystem under various circumstances are illustrated in FIGS. 5a–d. These signals are shown generally as negative pulse excursions from a reference voltage base, although it will be appreciated that the precise form and polarity of such electrical signals depends somewhat on circuitry utilized in the drop detection subsystem.

FIG. 5a illustrates three different waveforms which occur when drip chambers having cannula that form drops of different sizes are used. It can be seen that the waveforms exhibit progressively larger amplitudes and time durations as the drop size increases from 60 drops per milliliter to 20 drops per milliliter and, finally, to 10 drops per milliliter. The 10 drops per milliliter waveform shows a bifurcation caused by the drop momentarily acting as a lens when it interrupts the reference light beams, and thereby focusing the beams momentarily on the photocell. This largest drop also induces a smaller trailing drop which generates a small, delayed perturbation in the electrical signal from the drop detection subsystem. It should be noted that these variations in the waveforms occur with the drop sensor 10 correctly positioned on the drip chamber 12, about midway between the cannula 20 and the reservoir surface.

Figure 5B:
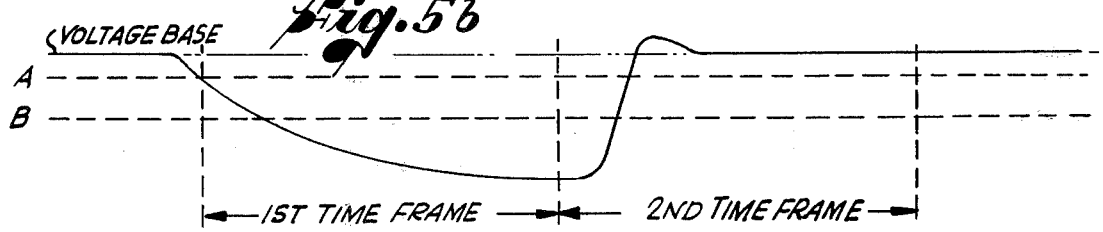
Figure 5C:
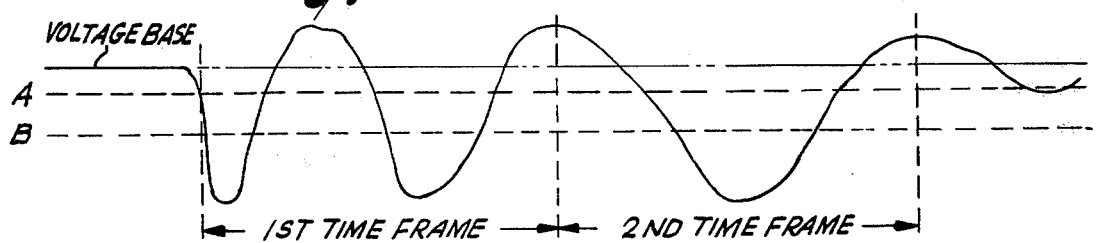

The releasable clamping feature of the drop sensor 10 allows medical personnel to incorrectly position the drop sensor on the drip chamber 12, thereby creating a second major source of variations in the waveforms of the electrical signals generated by the drop detection subsystem. For instance, FIG. 5b illustrates a waveform caused by incorrectly clamping the drop sensor 10 too near the upper end of the drip chamber 12 so that drops interrupt or partly occlude the reference beams while they form at the mouth of the cannula 20. The leading edge of this waveform is characterized by a very slow rise time and the pulse is abnormally long in duration, unlike the waveforms illustrated in FIG. 5a. Conversely, incorrectly positioning the drop sensor 10 too near or even below the surface of the fluid reservoir in the drip chamber 12 can result in an electrical signal with an oscillatory waveform as shown in FIG. 5c. The oscillation in the waveform results from the after-effects of splash and ripple on the reservoir surface after a drop has fallen, and it can be seen that the signal may extend above the reference voltage base if the reference beams are directed at the reservoir surface.

Irregularities in drop detection can occur even if the drop sensor is correctly positioned. For instance, FIG. 5d illustrates the waveform of the electrical signal typically generated by the drop detection subsystem when the drip chamber 12 is tilted such that the drops fall along a path very near the side of the drip chamber, thereby occluding a smaller portion of the reference beams than is occluded when the drops fall through the center of the drip chamber.

Figure 5D:
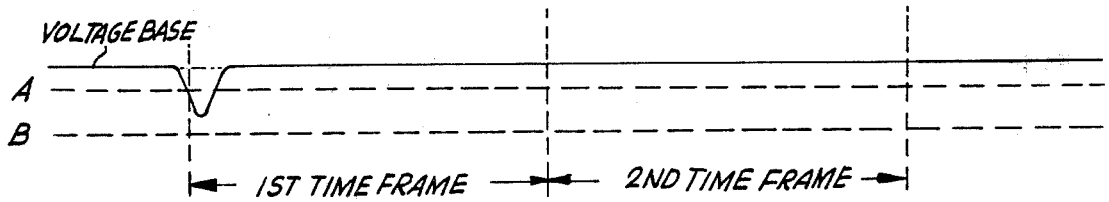

Each of the electrical signal waveforms illustrated in FIGS. 5b–d could result in erroneous drop flow rate detection unless corrective steps are taken. For example, depending on the nature of the circuitry which utilizes the illustrated electrical signals, FIG. 5b could result in the falling drop not being detected by circuitry that can be triggered only by a pulse of sufficiently fast rise time. In the case of the waveform shown in FIG. 5c, the parenteral administration device may erroneously perceive the occurrence of one falling drop for each oscillation. Finally, the pulse waveform of FIG. 5d might not trigger the circuitry of the parenteral administration device at all because of its inadequate amplitude. The circumstances producing each of the foregoing abnormal waveforms, however, can be corrected by adjusting the position of the drop sensor 10 or the drip chamber 12, or both, assuming some indication of the positioning error is provided to medical personnel. In the case of the bifurcated waveform shown in FIG. 5a which is sometimes produced by a large drop, no adjustment of the drop sensor 10 or drip chamber 12 is indicated, although this waveform should not be interpreted as a pair of falling drops.

The drop discriminator system of the present invention is effective to analyze the waveforms of the electrical signals that are generated by the drop detection subsystem to determine conformity with prescribed waveform characteristics expected from acceptable drop detection. Referring again to FIG. 3, the present invention involves interposing a waveform analysis subsystem 35 between the drop detection subsystem and the particular parenteral administration device being utilized, denoted as a fluid flow control subsystem 37 in the drawing, to perform the foregoing analysis and to trigger appropriate alarms via an alarm subsystem 39 if intolerable drop detection irregularities are present. The specific waveform analysis performed by a presently preferred embodiment will be understood from a description of the operation of the combined block diagram and electrical schematic shown in FIG. 4.

The electrical signal generated by the drop detection subsystem is provided over line 40 to first and second voltage discriminators 42 and 44, respectively, connected in parallel for evaluation of the amplitude of this electrical signal. These discriminators compare the incoming signal with prescribed voltage amplitude thresholds and produce a "true" output signal if their inputs exceed their respective thresholds.

The first voltage discriminator 42 has a relatively low amplitude threshold in comparison with the threshold of the second voltage discriminator 44. Since minor perturbations in the electrical signals generated by the drop detection subsystem are to be expected and can be tolerated without significant loss of reliability in the detection of drop flow, the threshold of the first voltage discriminator 42 is chosen to respond only to an electrical signal indicating the actual occurrence of drop flow in the drip chamber 12. For convenience, drop flow activity which sufficiently interrupts the drop sensor reference beams to cause an electrical signal from the drop detection subsystem of greater amplitude than the threshold of the first voltage discriminator 42 will be termed a "drop event".

Upon the occurrence of a drop event as so defined, the output of the first voltage discriminator 42 is effective to initiate first and second successive time frames, in the manner described below, for evaluation of the amplitude and time duration characteristics of the electrical signal representing the drop event. During the first time frame, the threshold of the second voltage discriminator 44 is utilized as the minimum voltage amplitude expected from acceptable detection of the drop event. Conversely, during the second time frame, this same threshold is utilized as the maximum voltage amplitude which will be tolerated of acceptable detection. In the presently preferred embodiment, the threshold of the second and first voltage discriminators, i.e., their excursion from the voltage base, shown as levels B and A in the FIG. 5 waveform, respectively, are chosen to have a ratio of approximately 3 to 1.

Specifically, upon detection of a drop event, the "true" output of the first voltage discriminator is directed over line 45 to the upper half of a flip-flop 46, hereinafter termed the "drop flip-flop", to record the occurrence of the drop event. The drop flip-flop 46 will remain in this state until the end of the second time frame, at which time it will be reset to its original condition. The output of the upper half of drop flip-flop 46 is directed over line 47 to the input of a first timer 48. The leading edge of a "true" output from the drop flip-flop 46 triggers generation of a "one-shot" output pulse of predetermined duration from the first timer 48 over line 49 to the input of a second timer 50 and to one input of an AND gate 51. The second timer 50 is a similar "one-shot" pulse generator, which is triggered by the trailing edge of the output pulse from the first timer 48. The output pulse from the first timer 48 and the second timer 50 are utilized as the first time frame and the second time frame, respectively. In the presently preferred embodiment, these times frames, identified in FIGS. 5b-d, are chosen to be equal 70 millisecond periods.

For ease of explanation, no attempt has been made in the block diagram of the presently preferred embodiment to adhere rigidly to consistent signal polarities between the various elements of the system. It will be understood by one of ordinary skill in the art that inverters may have to be inserted in various lines to correct apparent inconsistencies in signal polarities. Also, certain elements in the block diagram are responsive only to trigger inputs and, where applicable, these elements will be described herein as being responsive to leading or trailing edges of the appropriate pulse input signals.

The output of the upper half of drop flip-flop 46 is also directed over line 47 to the upper half of a second flip-flop 52. The leading edge of a "true" pulse from the drop flip-flop 46 sets flip-flop 52 to its "true" state. The state of the upper half of flip-flop 56 is utilized to store the decision as to the acceptability of the drop detection event throughout the waveform evaluation, and it will be referred to as the "decision flip-flop". Setting the upper half of decision flip-flop 52 to its "true" state is an indication that the electrical signal from the drop detection subsystem is initially considered unacceptable in the first time frame, pending further evaluation.

The output of the second timer 50 is directed simultaneously over line 53 to a counter 54 and another AND gate 55. Counter 54 is incremented one count by the trailing edge of the output pulse from the second timer 50 and, therefore, it will be apparent that its count coincides with the total number of drop events that have been evaluated. Therefore, counter 54 will be referred to as the "event counter". The output of the second timer 50 is also directed over line 53 as an input to the lower half of the drop flip-flop 46 and as an output signal to the fluid flow control subsystem. The pulse from the second timer 50 provides an indication of the flow of a single drop to the parenteral administration device and the trailing edge of this pulse resets the drop flip-flop 46 in preparation for evaluation of the next drop event.

The second voltage discriminator 44 directs its output simultaneously to the other inputs of both AND gates 51 and 55. The output of AND gate 51 is directed over line 56 as an input to the lower half of the decision flip-flop 52 and, similarly, the output of AND gate 55 is directed as an input to the upper half of the decision flip-flop over line 57. It can be seen that AND gate 51 is enabled throughout the first time frame by the output pulse from the first timer 48, and AND gate 55 is enabled throughout the second time frame by the output pulse from the second timer 50. Hence, AND gate 51 can be gated "on" by a "true" output from the second voltage discriminator 44 only during the first time frame, while AND gate 55 can be similarly gated "on" only during the second time frame.

The operation of this portion of the waveform analysis subsystem will now be understood. When the amplitude of the electrical signal from the drop detection subsystem exceeds the threshold of the first voltage discriminator, i.e., a drop event occurs, the drop flip-flop 46 is set, which triggers an output pulse from the first timer 48 and sets the decision flip-flop 52 to its "true" state. During this first time frame, AND gate 51 is enabled, so that it will be gated "on" if a "true" output is provided by the second voltage discriminator. This occurrence would indicate that the amplitude of the electrical signal from the drop detection subsystem had exceeded the threshold of the second voltage discriminator 44 during this first time frame. Under that circumstance, the decision flip-flop 52 would be reset to its "false" state, indicating that the quality of drop detection is considered acceptable from the standpoint of first time frame evaluation. In the absence of a signal from the second voltage discriminator 44, the decision flip-flop 52 will not be reset during the first time frame, resulting in a decision that the quality of the drop detection is unacceptable.

It should be noted that if the decision flip-flop 52 is reset to its "false" state during the first time frame, the waveform analysis subsystem will not respond to any further waveform characteristics of the electrical signal from the drop detection subsystem until the second time frame. On the other hand, if the amplitude of this electrical signal does not exceed the threshold of the second voltage discriminator 44 during the first time frame, the decision flip-flop 52 will not be reset to its "false" state, with the result that the quality of the drop detection will automatically be determined as unacceptable at the end of the second time frame.

As noted above, the second time frame is initiated by the trailing edge of the output pulse from the first timer 48. During the second time frame, AND gate 55 is enabled by the second timer 50 so that it can be gated "on" by a "true" output signal from the second voltage discriminator should the amplitude of the electrical signal from the drop detection subsystem prove excessive. In such an event, a "true" output from AND gate 55 will set the decision flip-flop 52 to its "true" state again, assuming it had been reset during the first time frame, to indicate unacceptability of drop detection from the standpoint of second time frame evaluation. Of course, if the decision flip-flop 52 had not been reset to its "false" state during the first time frame, it would already be in the "true" state.

Hence, it can be seen that once a drop event occurs, the quality of the drop detection is determined to be acceptable only if the amplitude of the electrical signal from the drop detection subsystem exceeds the threshold of the second voltage discriminator during the first time frame and is less than this same threshold throughout the second time frame. In other words, if the amplitude of the electrical signal from the drop detection subsystem does not attain sufficient amplitude during the first time frame or exhibits excessive amplitude during the second time frame, the quality of the drop detection is considered unacceptable. Referring now to the waveforms of FIG. 5, it will be apparent that the drop discriminator system of the present invention is effective to determine that each of the waveforms illustrated in FIGS. 5b–d represent unacceptable drop detection, while each of the waveforms of FIG. 5a are acceptable. It will also be apparent that, in the case of the oscillatory waveform of FIG. 5c and the bifurcated waveform of FIG. 5a, the occurrence of only one falling drop is communicated to the fluid flow control system over line 53 by the output pulse from the second timer.

For instance, the waveforms of FIGS. 5b and c will be seen to have acceptable amplitudes during the first time frame, but exceed the threshold of the second voltage discriminator 44 during the second time frame. Hence, in both instances, these signals will be recorded as unacceptable drop detection events. Under the circumstances shown by the waveform in FIG. 5d, threshold B of the second voltage discriminator 44 will never be exceeded during the first time frame so that the decision flip-flop 52 will be in its "true" state at the end of the second time frame. It will also be apparent that all of the waveforms of FIG. 5a, including the bifurcated waveform resulting from a large drop, will be correctly determined to be an acceptable drop detection, since each signal occurs entirely within the first time frame.

In order to allow some tolerance for the occurrence of occasional drop detections of unacceptable quality, the waveform analysis subsystem is not effective to trigger the alarm subsystem until a predetermined number of unacceptable drop detections has occurred. It is known, for instance, that the intravenous set will be occasionally jiggled or moved during use, possibly resulting in an electrical signal waveform like those of FIGS. 5b–d. It would not be desirable to trigger the alarm subsystem and thereby shut off the parenteral administration device for such a transient occurrence.

Accordingly, two counters are provided to record the total number of drop events that are analyzed and to record the portion of the total which are determined to be unacceptable, respectively. Event counter 54, as noted above, records the total number of drop events, since it is incremented one count by the trailing edge of the output pulse from the second timer 50 at the end of the second time frame. The number of unacceptable drop detections is recorded in a counter 58 which receives its input through an AND gate 59 controlled by the output of the upper half of decision flip-flop 52 over line 60 and the output of the second timer over line 53. Counter 58 will be incremented one count on the trailing edge of the output pulse from the second timer 50 at the end of the second time frame if the upper half of decision flip-flop 52 has been set to its "true" state at that time. As discussed above, a "true" state in the upper half of decision flip-flop 52 indicates that the drop detection event is considered unacceptable.

In the preferred embodiment, event counter 54 has a capacity of 16 and counter 58 has a capacity of 5. In accordance with the invention, this allows tolerance of up to 4 unacceptable drop detection events in a total set of 16, before the output of counter 58 triggers the alarm subsystem. Thus, the drop discriminator system will not alarm unnecessarily when the parenteral administration device is moved or jiggled briefly in normal use.

After evaluation of 16 successive drop detection events, event counter 54 overflows on line 61 through an OR gate 62 and the "true" output of this OR gate resets counter 58 over line 63. The waveform analysis subsystem can then begin evaluation of the next set of 16 drop events, and so on.

A reset generator 64, a reset flip-flop 65, and OR gate 62 function to inhibit operation of the waveform analysis subsystem during startup of the parenteral administration device. It is desirable to inhibit the waveform analysis subsystem during startup because drop flow at this time is characteristically erratic, for instance, due to initial filling of the feeding tube 22 and the reservoir in the drip chamber 12 with liquid from the bottle 18. Startup is initiated by the reset generator (which is normally triggered by the start switch on the parenteral administration device, not shown) producing a pulse over line 66 to the upper half of reset flip-flop 65, to a reset input of event counter 54 and, through OR gate 62, to the reset input of counter 58 over line 63. The output of the upper half of reset flip-flop 65 is directed over line 67 to an input on the lower half of decision flip-flop 52, thereby clamping the upper half of the decision flip-flop in its "false" state. This condition is maintained until event counter 54 has been incremented through one full cycle of 16 counts and its overflow signal on line 61 sets the lower half of the reset flip-flop 65 to a "true" state, thereby releasing the decision flip-flop 52 to respond to the detection of an unacceptable drop event.

Note should be made that the selection of the particular thresholds for the voltage discriminators and the durations of the time frames in the preferred embodiment, as well as the capacities of the counters, were made with reference to a particular drop sensor and accompanying drop detection subsystem circuitry for effective operation with intravenous sets producing drops in the range from 60 drops per milliliter to 10 drops per milliliter. Of course, these parameters depend upon the particular drop sensor configuration and components, associated drop detection subsystem circuitry and the range of drop sizes with which the drop discriminator system is designed to operate.

The new and improved drop discrimination system of the present invention insures accurate and reliable detection of drop flow by effectively discovering defective drop detection events. The system minimizes the possibility that incorrect positioning of the drop sensor on the drip chamber or tilting of the drip chamber will continue uncorrected. The system is quick to inform medical personnel of any irregularities in drop detection which might pose a hazard to the patient.

It will be apparent from the foregoing that, while particular forms of the invention have been illustrated and described, various modifications can be made without departing from the spirit an scope of the invention.

I claim:

1. In a drop detection system for use with fluid flow control apparatus, in the parenteral administration of liquids through a feeding tube from a liquid source to a patient, the combination comprising:
    first means for generating electrical signals in response to detection of drop flow activity;
    second means for receiving said electrical signals to determine the occurrence of individual drops;
    third means, responsive to said second means, for providing drop signals indicative of drop flow events to the fluid flow control apparatus;
    fourth means, also responsive to said second means, for qualitatively evaluating the waveforms of each of said electrical signals representing individual drop configurations to determine their conformity with prescribed waveform characteristics, whereby proper drop flow events may be qualitatively distinguished from improper drop flow events; and
    fifth means, responsive to the electrical output of said fourth means, for providing an indication of nonconformity in the waveform characteristics of a prescribed number of said electrical signals to determine proper operation of the fluid flow control apparatus.

2. A combination as set forth in claim 1, wherein said fourth means includes means for evaluating the amplitude of each of said electrical signals to determine their conformity with prescribed amplitude characteristics.

3. A combination as set forth in claim 2, wherein said fourth means includes means for evaluating the amplitude of each of said electrical signals by comparing said amplitude with a plurality of prescribed amplitude levels.

4. A combination as set forth in claim 2, wherein said second means provides an indication of nonconformity in the amplitudes of a prescribed number of said electrical signals.

5. A combination as set forth in claim 1, wherein said fourth means includes means for evaluating the time duration of each of said electrical signals to determine their conformity with prescribed time duration characteristics.

6. A combination as set forth in claim 5, wherein said fourth means includes means for evaluating the time duration of each of said electrical signals by comparing said time duration with a plurality of prescribed time duration frames.

7. A combination as set forth in claim 5, wherein said second means provides an indication of nonconformity in the time durations of a prescribed number of said electrical signals.

8. A combination as set forth in claim 1, wherein said fourth means includes means for evaluating both the amplitude and the time duration of each of said electrical signals to determine their conformity with prescribed amplitude and time duration characteristics, respectively.

9. A combination as set forth in claim 8, wherein said fourth means includes means for evaluating the amplitude and the time duration of each of said electrical signals by comparing said amplitude and said time duration with a plurality of prescribed amplitude levels and a plurality of prescribed time durations, respectively.

10. A combination as set forth in claim 8, wherein said second means provide an indication of nonconformity in the amplitudes and time durations of a prescribed number of said electrical signals.

11. In a drop detection system for use with a fluid flow control apparatus, in the parenteral administration of liquids through a feeding tube from a liquid source to a patient, the combination comprising:

first means for generating electrical signals in response to detection of drop flow activity;

second means for receiving said electrical signals to determine the occurrence of individual drops;

third means, responsive to said second means, for providing drop signals indicative of drop flow events to the fluid flow control apparatus;

fourth means for qualitatively evaluating the amplitude of each of said electrical signals representing individual drop flow events during a prescribed time frame to determine their conformity with prescribed amplitude characteristics during said time frame, whereby proper drop flow events may be qualitatively distinguished from improper drop flow events; and fifth means, responsive to the electrical output of said fourth means, for providing an indication of nonconformity in the waveform characteristics of a prescribed number of said electrical signals to determine proper operation of the fluid flow control apparatus.

12. A combination as set forth in claim 11, wherein said fourth means includes means for evaluating the amplitude of each of said electrical signals during a plurality of successive time frames to determine their conformity with prescribed amplitude characteristics.

13. A combination as set forth in claim 11, wherein said fourth means includes means for evaluating the amplitude of each of said electrical signals by comparing said amplitude with a plurality of prescribed amplitude levels.

14. A combination as set forth in claim 13, wherein said fourth means includes means for evaluating the amplitude of each of said electrical signals during a plurality of successive time frames to determine their conformity with prescribed amplitude characteristics.

15. In a drop detection system for use with fluid flow control apparatus, in the parenteral administration of liquids through a feeding tube from a liquid source to a patient, the combination comprising:

first means for generating electrical signals in response to detection of drop flow activity;

second means for receiving said electrical signals to determine the occurrence of individual drops;

third means, responsive to said second means, for providing drop signals indicative of drop flow events to the fluid flow control apparatus;

fourth means for qualitatively evaluating the time duration of each of said electrical signals representing individual drop flow events within a prescribed amplitude range to determine their conformity with prescribed time duration characteristics, whereby proper drop flow events may be qualitatively distinguished from improper drop flow events; and fifth means, responsive to the electrical output of said forth means, for providing an indication of nonconformity in the waveform characteristics of a prescribed number of said electrical signals to determine proper operation of the fluid flow control apparatus.

16. A combination as set forth in claim 15, wherein said fourth means includes means for evaluating the time duration of each of said electrical signals within a plurality of prescribed amplitude ranges to determine their conformity with prescribed time duration characteristics.

17. A combination as set forth in claim 15, wherein said fourth means includes means for evaluating the time duration of each of said electrical signals by comparing said time duration with a plurality of prescribed time frames.

18. In a drop detection system for use with fluid flow control apparatus, in the parenteral administration of liquids through a feeding tube from a liquid source to a patient, the combination comprising:

sensing means for detecting drop flow activity;

means responsive to said sensing means for generating electrical signals representative of the individual drops detected;

means for qualitatively evaluating the waveforms of each of said electrical signals to establish the occurrence of individual drop flow events, whereby individual drop flow events may be qualitatively distinguished from artifacts, and for providing drop signals indicative of individual drop flow events to the fluid flow control apparatus;

amplitude discrimination means for qualitatively evaluating the amplitude of each of said electrical signals representing individual drop configurations to determine their conformity with prescribed amplitude characteristics, whereby proper drop flow events may be qualitatively distinguished from improper drop flow events;

timing means for establishing a time frame during which the amplitude of each of said electrical signals representing individual drop configurations is evaluated by said amplitude discrimination means; and means responsive to qualitative evaluation of said drop flow events, for determining proper operation of the fluid flow control apparatus.

19. A combination as set forth in claim 18, and further including means for initiating said timing means in response to said amplitude discrimination means.

20. A combination as set forth in claim 18 wherein said timing means includes means for establishing a plurality of successive time frames during which the amplitude of each of said electrical signals is evaluated by said amplitude discrimination means.

21. A combination as set forth in claim 18, and further including:

indicator means for providing an indication of nonconformity in the amplitudes of a prescribed number of said electrical signals.

22. A method for determining the quality of the detection of drop flow activity during the parenteral administration of liquids through a feeding tube from a liquid source to a patient, comprising the steps of:

generating electrical signals in response to the detection of individual drops; and qualitatively evaluating the waveforms of each of said electrical signals representing individual drop configurations to determine their conformity with prescribed waveform characteristics, whereby proper drop flow events may be qualitatively distinguished from improper events and artifacts.

23. A method as set forth in claim 22, comprising the additional step of:

indicating a lack of conformity in the waveforms of a predetermined number of said electrical signals.

24. A method for evaluating the quality of the detection of drop flow activity during the parenteral administration of liquids through a feeding tube from a liquid source to a patient, comprising the steps of:
  generating electrical signals in response to the detection of individual drops; and
  qualitatively evaluating the amplitudes of each of said electrical signals representing individual drop configurations during time frames of predetermined duration to determine the conformity of said electrical signals with prescribed waveform characteristics, whereby proper drop flow events may be qualitatively distinguished from improper events and artifacts.

25. A method as set forth in claim 24, and further including the step of:
  indicating a lack of conformity in the amplitudes of a predetermined number of said electrical signals.

26. In a drop detection system for use with fluid flow control apparatus, in the parenteral administration of liquids through a feeding tube from a liquid source to a patient, the combination comprising:
  sensing means for detecting drop flow activity;
  means responsive to said sensing means for generating electrical signals representative of the individual drops detected;
  first discriminator means for qualitatively determining whether the amplitude of each of said electrical signals exceeds a first level, whereby the occurrence of an individual drop flow event is detected;
  second discriminator means for qualitatively determining whether the amplitude of each of said electrical signals representing an individual drop configurations exceeds a second level greater than said first level;
  timing means responsive to said first discriminator means for establishing first and second successive time frames during which the amplitude of each of said electrical signals is compared with said second level; and
  means responsive to qualitative evaluation of said drop flow events, for determining proper operation of the fluid flow control apparatus.

27. A combination as set forth in claim 26, and further including:
  indicator means for indicating whether the amplitude of each of said electrical signals representing an individual drop flow event does not exceed said second level during said first time frame or does exceed said second level during said second time frame.

28. A combination as set forth in claim 26, and further including:
  first counting means for counting each electrical signal with an amplitude exceeding said first level, whereby a count of individual drop flow events is provided; and
  second counting means for counting each electrical signal counted by said first counting means and having an amplitude which also does not exceed said second level during said first time frame, whereby a count is provided of improper drop flow events as distinguished from proper drop flow events.

29. A combination as set forth in claim 28, and further including:
  alarm means responsive to said first and second counting means for triggering an alarm when the ratio of the count in said first counting means to the count in said second counting means exceeds a prescribed level.

30. A combination as set forth in claim 29, including means for resetting both said first counting means and said second counting means if the count in said first counting means exceeds a prescribed level.

31. A combination as set forth in claim 26, further including:
  first counting means for counting each electrical signal with an amplitude exceeding said first level, whereby a count of individual drop flow events is provided; and
  second counting means for counting each electrical signal counted by said first counting means and having an amplitude which also exceeds said second level during said second time frame, whereby a count is provided of improper drop flow events as distinguished from proper drop flow events.

32. A combination as set forth in claim 31, further including:
  alarm means responsive to said first and second counting means for triggering an alarm when the ratio of the count at said first counting means to the count at said second counting means exceeds a prescribed level.

33. A combination as set forth in claim 32, including means for resetting both said first counting means and said second counting means if the count in said first counting means exceeds a prescribed level.

34. In a drop detection system for use with fluid flow control apparatus, in the parenteral administration of liquids through a feeding tube from a liquid source to a patient, the combination comprising:
  first means for generating electrical signals in response to detection of individual drops;
  second means for qualitatively evaluating the waveforms of each of said electrical signals representing individual drop configurations to determine their conformity with prescribed waveform characteristics, whereby proper drop flow events may be qualitatively distinguished from improper events and artifacts; and
  third means, responsive to the electrical output of said second means, for determining proper operation of the fluid flow control apparatus.

35. A combination as set forth in claim 34, wherein said second means includes means for evaluating the amplitude of each of said electrical signals to determine their conformity with prescribed amplitude characteristics.

36. A combination as set forth in claim 35, wherein said second means includes means for evaluating the amplitude of each of said electrical signals by comparing said amplitude with a plurality of prescribed amplitude levels.

37. A combination as set forth in claim 35, wherein said second means includes means for providing an indication of non-conformity in the amplitudes of a prescribed number of said electrical signals.

38. A combination as set forth in claim 34, wherein said second means includes means for evaluating the time duration of each of said electrical signals to determine their conformity with prescribed time duration characteristics.

39. A combination as set forth in claim 38, wherein said second means includes means for evaluating the time duration of each of said electrical signals by comparing said time duration with a plurality of prescribed time duration frames.

40. A combination as set forth in claim 38, wherein said second means includes means for providing an indicacion of non-conformity in the time durations of a prescribed number of said electrical signals.

41. A combination as set forth in claim 34, wherein said second means includes means for evaluating both the amplitude and the time duration of each of said electrical signals to determine their conformity with prescribed amplitude and time duration characteristics, respectively.

42. A combination as set forth in claim 41, wherein said second means includes means for evaluating the amplitude and the time duration of each of said electrical signals by comparing said amplitude and said time duration with a plurality of prescribed amplitude levels and a plurality of prescribed amplitude levels and a plurality of prescribed time durations, respectively.

43. A combination as set forth in claim 41, wherein said second means include means for providing an indication of non-conformity in the amplitudes and time durations of a prescribed number of said electrical signals.

* * * * *

UNITED STATES PATENT AND TRADEMARK OFFICE
CERTIFICATE OF CORRECTION

PATENT NO. : 4,181,130
DATED : January 1, 1980
INVENTOR(S) : Wilber H. Bailey

It is certified that error appears in the above–identified patent and that said Letters Patent are hereby corrected as shown below:

Claim 42, Column 18, Line 6: "and a plurality of prescribed amplitude levels" should be deleted.

Claim 40, Column 17, Line 5: "indicacion" should be spelled "indication".

Signed and Sealed this

Twenty-ninth Day of July 1980

[SEAL]

Attest:

SIDNEY A. DIAMOND

Attesting Officer

Commissioner of Patents and Trademarks